US005710315A

United States Patent [19]
Gallagher

[11] Patent Number: 5,710,315
[45] Date of Patent: *Jan. 20, 1998

[54] MONOMER RECOVERY PROCESS FOR CONTAMINATED POLYMERS

[75] Inventor: Francis Glenn Gallagher, Wilmington, Del.

[73] Assignee: E. I. Du Pont de Nemours and Company, Wilmington, Del.

[*] Notice: The term of this patent shall not extend beyond the expiration date of Pat. No. 5,532,404.

[21] Appl. No.: 668,760

[22] Filed: Jun. 24, 1996

Related U.S. Application Data

[63] Continuation-in-part of Ser. No. 250,391, May 27, 1994, Pat. No. 5,532,404.

[51] Int. Cl.$^6$ .................................................. C07C 67/48
[52] U.S. Cl. ................................................. 560/78; 560/96
[58] Field of Search ........................ 560/78, 96; 521/40, 521/48, 485; 528/481, 492, 496, 503

[56] References Cited

U.S. PATENT DOCUMENTS

| | | | |
|---|---|---|---|
| 2,884,443 | 4/1959 | Laudenbach et al. | 260/475 |
| 3,037,050 | 5/1962 | Helsenberg et al. | 260/475 |
| 3,321,510 | 5/1967 | Lotz et al. | 260/475 |
| 3,544,622 | 12/1970 | England | 260/515 |
| 3,776,945 | 12/1973 | Ligorati et al. | 260/475 D |
| 3,952,053 | 4/1976 | Brown, Jr. et al. | 260/525 |
| 4,355,175 | 10/1982 | Pusztaszeri | 562/483 |
| 4,542,239 | 9/1985 | Lamparter et al. | 562/487 |
| 4,609,680 | 9/1986 | Fujita et al. | 521/48 |
| 5,051,528 | 9/1991 | Naujokas et al. | 560/78 |
| 5,481,024 | 1/1996 | Hertenstein et al. | 560/78 |
| 5,532,404 | 7/1996 | Gallagher | 560/78 |

FOREIGN PATENT DOCUMENTS

| | | | |
|---|---|---|---|
| 0 484 963 | 5/1992 | European Pat. Off. | C07C 69/82 |
| 54-84525 | 7/1979 | Japan | C07C 121/43 |
| 58-020951 | 4/1983 | Japan | C07C 69/82 |
| 1 172 997 | 3/1969 | United Kingdom | C07C 87/14 |

*Primary Examiner*—José G. Dees
*Assistant Examiner*—Barbara Badio

[57] ABSTRACT

An improved process for recovering depolymerization products from polymers such as polyesters, polyamides, and polyesteramides, especially when the starting polymer content is less than about 98%. The depolymerization and vapor phase recovery of monomers and other reaction products are conducted in the presence of a solid support.

20 Claims, No Drawings

MONOMER RECOVERY PROCESS FOR CONTAMINATED POLYMERS

CROSS-REFERENCE TO RELATED APPLICATION

This is a continuation-in-part of my application Ser. No. 08/250,391 filed May 27, 1994, now allowed and scheduled to issue as U.S. Pat. No. 5,532,404 on Jul. 2, 1996.

BACKGROUND OF THE INVENTION

This invention relates to recovery of reaction products (i.e., monomers and other depolymerization products) from contaminated plastics. Specifically, this invention relates to processes for recovering monomers from polymers having a desired polymer content below about 98%.

TECHNICAL BACKGROUND OF THE INVENTION

The inadequate treatment of waste which is landfilled, and the increasing percentage of nondegradable materials, including plastics in municipal solid waste streams, have increased the cost of solid waste disposal and further stimulated public pressure to recycle nondegradable plastic material.

Over the years there have been many technological developments in the field of production and use of polymers. Various additives modifiers, comonomers, copolymers, and fillers have been incorporated into polymers to improve characteristics such as strength and temperature resistance, and to thereby meet the needs of more specialized applications. Polymers have also been used in conjunction with other materials to make complex systems and composites where separation of the individual materials would be difficult. In addition to material added in the manufactured polymer, post-consumer sold waste (i.e., that used by consumers and then discarded or placed into the solid waste) usually contains contamination introduced during consumer use of the article or during the collection process. The presence of these contaminants, and materials incorporated during manufacture, have limited the effectiveness of post-consumer plastic recycling. The problem is one of initial low purity of the desired plastic and the necessity to process a wide range of other materials that may be present.

Polyesters and polyamides, for example, may be recycled by various methods to yield useful polymers, oligomers and monomers. Traditional chemical recovery techniques include hydrolysis, glycolysis and methanolysis for polyesters, and hydrolysis and ammonolysis for polyamides. For polyesters, these methods are most often combined with an initial depolymerization step, which is accomplished by heating and/or dissolving the polymer in oligomers, monomers (such as ethylene glycol), or water.

Hydrolysis involves treating the starting polymer with water and heat. Complete depolymerization will yield monomers (e.g., terephthalic acid and ethylene glycol (EG) for polyethylene terephthalate (PET); and hexamethylene diamine and adipic acid for nylon 6,6), which can then be polymerized. For PET, additional additives such as salts, NaOH, $H_2SO_4$, and $NH_3OH$, are sometimes used to enhance the process. See U.S. Pat. Nos. 4,355,175, 3,544,622, 3,952,053 and 4,542,239, respectively. Additionally, hydrolysis, specifically steam treatment, can by used in conjunction with other treatments discussed below, see U.S. Pat. No. 3,321,510.

Another recovery method for PET, glycolysis, is accomplished by using a glycol, e.g. EG or 1,4-butanediol (BDO), to break down the polymer. This has been done in the liquid phase, and usually employs heat and pressure. Glycolysis of PET with ethylene glycol yields bis-β-hydroxyethyl terephthalate (BHET) which is then usually filtered to remove impurities and polymerized, see U.S. Pat. No. 4,609,680. Glycolysis can be combined with a second step, e.g., methanolysis, see U.S. Pat. No. 3,321,510.

The third method for polyesters, alcoholysis, e.g., methanolysis, breaks down the polymer back to its monomers. Conventional methanolysis generally operates using a polymer melt in which superheated methanol is bubbled through the mixture. See, for example, EPO Patent Application 0484963A3 and U.S. Pat. No. 5,051,528. Methanolysis can optionally include the use of catalysts to enhance the recovery rate, see, for example, U.S. Pat. Nos. 3,776,945 and 3,037,050, as well as the use of organic solvents, see U.S. Pat. No. 2,884,443. Methanolysis can be used in conjunction with various initial depolymerization methods, for example, dissolving the polymer in its oligomers, see U.S. Pat. No. 5,051,528; depolymerizing using EG, see Japanese Patent No. 58,020,951 B4; or depolymerizing using water, see U.S. Pat. No. 3,321,510. After alcoholysis of PET with methanol and recovering the monomers, an additional refining step may be used to separate and purify the DMT from EG. This can be done by precipitation, distillation, or cystallization.

For polyamides, ammonolysis can be used to break down the polymer back to monomers. For example, Japanese Patent Application Publication 54-84,525 (1979) describes a process to obtain the monomers 6-aminocapronitrile and caprolactam which is accomplished by treating molten polycaproamide (nylon 6) at elevated temperature and pressure with ammonia gas. British Patent 1,172,997 discloses the conversion of a polyamide into monomeric compounds by heating the polyamide (nylon 6 and nylon 6,6) with ammonia in the presence of hydrogen and a hydrogenation catalyst. With nylon 6,6 the monomers obtained are hexamethylene diamine and hexamethyleneimine and a small amount of unidentified material. With nylon 6, the monomers obtained are hexamethylenediamine, hexamethyleneimine and N-(6-aminohexyl)-hexamethyleneimine.

SUMMARY OF THE INVENTION

This invention provides a process for recovering volatile reaction products (e.g., monomers and other depolymerization products) from a reaction mass that comprises a starting polymer which is at least one member of the group consisting of polyesters, polyamides, and copolyesteramides having about 2% to 70% by weight of non-polymer contaminants, which process comprises:

(a) depolmerizing the polymer by means of a depolymerization agent to yield volatile reaction products;

(b) vapor-phase stripping the volatile reaction products, to yield a stripping agent/product distillate;
  wherein said reaction mass in said depolymerizing and stripping comprises from about 5% to about 99% by weight of the reaction mass of a solid support, which solid support is solid under the conditions of steps (a) and (b) and forms a suspended bed, either the quantity alone or both the quantity and the rate of recovery of reaction products being enhanced over that or those obtained in the absence of said solid support; and (c) recovering the reaction products from the stripping agent/product distillate while leaving non-volatile residue material with the support material.

The depolymerization and stripping process is conducted within a temperature range of about 140° C. to about 350°

C. Typical pressure for the reaction is about 5000 psig (34,475 kPa) or less.

DETAILED DESCRIPTION OF THE INVENTION

The present invention addresses the following concerns:

(1) The content of desired polymer in post consumer waste plastic varies and is typically less than about 98%, which decreases the yield of conventional recovery methods.

(2) The non-polymer contaminants vary in type and amount.

(3) To maximize the yield of recovered products while minimizing the quantity of byproduct, the residue following extraction of desired polymer optimally should have a low level (<50%) of desired polymer remaining.

(4) The polymer recovery process should be economical, minimizing the number of operations, supplemental material requirements, and material movement.

The novelty of the applicants' solution to these concerns consists in the use of a solid support matrix to aid the depolymerization and vapor phase stripping of the monomers for polymer recycling, specifically for polyester and polyamide recycling. The solid support matrix is used as the suspended bed in the reactor as described below.

Typical polyesters for treatment by the present process include, but are not limited to, polyethylene terephthalate, polypropylene terephthalate (PPT), poly(1,4-butylene) terephthalate (PBT), and copolyesters, including liquid crystal polymers (LCPs). Typical Polyamides include nylon 6 and nylon 6,6, and copolyamides. Mixtures of two or more of the aforementioned materials can be subjected to the improved depolymerization process of this invention.

By "starting polymer" (i.e., polymer contaminated with non-polymer contaminants) is meant any pre-consumer or post-consumer polymer having a content of the desired polymer below 98%. Such polymers include polyesters of dicarboxylic acids, polycarbonates, polyamides including aramids, and copolymers having both ester and amide repeating units. Broadly, the starting polymer will comprise repeat units derived from:

(a) at least one dicarboxylic acid and/or carbonic acid and at least one diol and/or a diamine; or (b) at least one hydroxycarboxylic acid and/or aminocarboxylic acid; or (c) at least one dicarboxylic acid and/or carbonic acid, at least one diol and/or diamine, and at least one hydroxycarboxylic acid and/or an aminocarboxylic acid.

By "non-polymer contaminants" is meant any material that is not the desired polymer. This includes additives, modifiers, comonomers, copolymers, and fillers incorporated during polymer preparation; as well as other material and polymers incorporated during article construction and contamination introduced during use or during collection. The process described herein is suitable for processing non-polymer contamination levels of about 2% to about 70%, by weight of the starting charge or feed.

By "starting polymer charge" is meant starting polymer loaded in a single batch, while "starting polymer feed" refers to starting polymer continuously fed to a reaction mass.

By "reaction products", herein is meant both a monomer capable of undergoing polymerization to make up the basic repeating unit of a polymer and any other product obtained from depolymerization of a polymer that can be chemically converted and subsequently polymerized. Examples of monomers that make up the basic repeating unit of a polymer are for polyesters, ethylene glycol and dimethyl terephthalate, and for nylon 6,6, hexamethylenediamine. An example of another product obtained from depolymerization of a polymer, which can be easily converted to a monomer and then polymerized is adiponitrile obtained from nylon 6,6.

Depolymerization of polyesters gives, among others, aliphatic, aromatic, and aliphatic-aromatic diols. For PET, common reaction products include ethylene glycol, dimethyl terephthalate, and bis-β-hydroxyethyl terephthalate. Other reaction products for polyesters in general, including LCPs based on polyesters, include dicarboxylic acids and their methyl or ethyl esters; for example, terephthalic acid, isophthalic acid, dimethyl isophthalate, 2,6-napthalenedicarboxylic acid, bibenzoic acid (4,4'-dicarboxydiphenyl), and oxybibenzoic acid (4,4'-dicarboxydiphenyl ether); $C_2$–$C_{16}$ diols, such as 1,3-propanediol, 1,4-butanediol, diethylene glycol, 1,3-dipropylene glycol, triethylene glycol, 1,3-tripropylene glycol, hydroquinone, biphenol (4,4'-dihydroxydiphenyl), oxybiphenyl (4,4'-dihydroxydiphenyl ether), bisphenol-A, 2-methylhydroquinone, 2-(t-butyl)hydroquinone, 2-phenylethylhydroquinone, 2-phenyl hydroquinone, resorcinol, and 2,6-dihydroxynaphthalene; as well as hydroxyacids, and their corresponding methyl and ethyl esters, such as 4-hydroxybenzoic acid, 6-hydroxy-2-naphthoic acid, 4-hydroxy-4'-carboxy diphenyl, and 4-hydroxy-4'carboxy-diphenyl ether.

For nylon 6 and nylon 6,6, reaction products include hexamethylenediamine, 5-cyanovaleramide, adiponitrile, caprolactam, 6-aminocaproamide, 6-aminocapronitrile, trimethylamine, dimethyl adipate, and 1,6-hexanediol.

By "volatile reaction product" is meant any monomer or product that has a sufficiently high vapor pressure to be stripped by a stripping gas at reaction temperatures and pressures. When operating continuously, the cost of recycling the stripping gas can be controlled by selecting operating conditions such that the concentration of reaction products in the stripping vapor is greater than about 1 weight % and preferably greater than about 10 weight %.

By "solid support" is meant a material which is solid under reaction conditions, which expands the volume of the reaction media and provides additional reaction surface area to improve gas/polymer and gas/oligomer contacting, and thus to improve the rate or extent of depolymerization and stripping processes. The solid support herein is preferably in the form of a plurality of inert particles which are solid under reaction conditions, which can be distributed substantially homogenously throughout the reaction mixture. Such particles provide a baffle-type system which supports the starting polymer and expands the volume of the reaction mixture. The expansion provides more gas/polymer and gas/oligomer contacting, thus improving the rate or extent of depolymerization and stripping processes.

Several performance criteria generally apply to the solid particles described above.

The first is that the mount of fines (i.e., very small particles that may be entrained with the gas, e.g., about 100 μm or less, should be no more than about 10% by weight of the total amount of solid support, and preferably less than about 1%. This reduces the amount of solids entrainment below the theoretical value, which can be calculated from known parameters such as particle size, particle shape, particle density, vapor density, vapor linear velocity, etc.

The second is that the combination of solid support integrity and agitation of the system should not produce a significant amount of new fines. Solid movement generally should be kept to a minimum so that fines production is minimized. If the solid support is glass fibers, no movement is preferred, and thus operating below fluidization velocities is desirable. Some movement still may be acceptable provided that fines production is minimal. Other solid systems, such as carpet backing, may tolerate higher agitation rates.

The third is that the gas must be able to pass through the solid support. For a mechanically agitated system, the solid support must be sufficiently free-flowing to provide such intimate contact. For stationary bed systems, a maximum pressure drop occurs across the static bed. Acceptable pressure drops in the instant invention are on the order of 1 to 100 psi per foot (22.6-2262 kPa per meter) of bed thickness. When the system is mechanically agitated, rather than fluidized, the geometry of agitation is more important than fluidization velocity, and pressure drop across the bed does not apply. See generally, M. Pell, *Gas Fluidization, Handbook of Powder Technology*, Vol. 8, Elsevier, N.Y., 1990, pp. 1-19, and Perry, R. H. et al., *Chemical Engineer's Handbook*, 6th Edition, McGraw-Hill, Inc., 1984, Chapter 20.

In one embodiment of the invention, the supporting material is a component of the starting material, specifically glass fibers or flakes in engineering resins or composites. Solid supports which are components of the starting material can be described as having two general structures. The first is where the solid is "in contact with or connected to" the polymer, which means in physical contact with the polymer. This can include physical mixtures, blends and woven fabrics. A second structure is where the solid is intimately mixed or "fused" to the polymer, which means physically adhered to the polymer without adhesive, usually having been melted, such as in engineering polymer articles. The latter group presents a more difficult recycling problem than the former.

Alternatively, solid support material can be added to the reaction mixture to produce the same supporting effect. Suitable materials include (1) inorganic materials such as glass (e.g., oxides of silicon and boron), carbon fibers, ceramics, and various minerals (e.g., mica, talc, calcium carbonate, wollastonite), (2) metals, (3) non-woven natural organic materials based on cellulose, hemicellulose, and lignin, among others, e.g., wood, (4) woven natural organic materials based on the materials in (3) above, e.g., burlap or jute carpet backing, and (5) polymers that do not melt or significantly react (i.e., less than about 5 weight percent reacts at processing conditions, such as aramids, e.g., Kevlar® and Nomex® (DuPont, Wilmington, Del.) when processing PET.

By "depolymerization agent" is meant a solid, liquid or gas that will react with a repeat linkage, e.g., ester, amide, carbonate or aramid linkages, to yield two product components, thus lowering the molecular weight and increasing the vapor pressure. For polyesters, the depolymerization agent can be a low molecular weight oligomer of a polyester, an alcohol, such as methanol, a monomer, an alkanediol, specifically ethylene glycol, an aromatic or aliphatic carboxylic acid (e.g., acetic acid), or a corresponding methyl or ethyl ester (e.g., methyl benzoate), an aromatic or aliphatic dicarboxylic acid or corresponding ester, or water. By "oligomer" is meant a low molecular weight form of a given polymer. When water, oligomers, or some diols or dicarboxylic acids are used as the depolymerization agents, the initial product is not highly volatile. Thus, a second agent, such as alcohol or diol, is needed to yield more easily volatilized products. In these cases, the depolymerization is conducted in two steps, wherein the first step lowers the molecular weight and the second step yields a volatile monomer. For polyamides, the depolymerization agent may be methanol, ethylene glycol, oligomer of a polyamide, monomer, water or ammonia. Use of ammonia as a final depolymerization agent for polyamides is particularly advantageous because it produces volatile products which may be easily separated from the reaction mass.

By "stripping agent" is meant a material which is a gas at reaction temperature and pressure which is able to carry away the volatile products of the process and which will not retard the depolymerization reaction. The stripping gas may be the depolymerization agent itself as long as such depolymerization agent yields a volatile product, (for example alcohols and alkane diols for PET or ammonia for nylon) or an inert gas, such as nitrogen. The stripping gas is passed through the reaction vessel and carries away the volatile monomers.

When the starting material is a mixture of starting polymers of different classes such as, for example, polyesters and polyamides or the starting polymer is a polyesteramide, it may be necessary to devise an appropriate process strategy. For example, one would have to decide whether the process should be run in separate stages, to first depolymerize one species and then the other, or in one stage. If in one stage, whether one should use different depolymerization agents and/or different stripping agents or select a depolymerization agent and a stripping agent that will be operable with both polyesters and polyamides. For example, methanolysis may work in some cases, where polyesters produce diols, hydroxyacid methyl esters, and dicarboxylic acid methyl esters, while polyamides produce N-methyl amines, diols, and methyl esters of carboxylic acids.

The method of this invention can be used to obtain a better recovery percentage of desired reaction products for these polymer materials than is obtainable through recovery methods that do not use applicants' solid support matrix. The present method is particularly suited for scrap resin with only modest desired polymer content, for example, glass fiber- or metal-reinforced engineering polymers, and for treating physical blends of post-consumer PET and polyethylene, which is common in beverage container recycling. Additionally, PET by-product from commercial facilities can be treated effectively, as well as composite structures such as, for example, carpet and fabric (e.g., cotton/polyester blends).

Traditional methods of polymer recycling are not as efficient as the present process in situations where the starting materials have a low level of desired polymer content. Typically, the by-product stream in these methods still contains a rather high polymer level and corresponding reaction product content, greater than about 50% and, therefore, suffers the loss of valuable reaction products with the increased by-product formation. This outcome is compounded when the starting material is a highly fiber-filled polymer since it is even more difficult to separate the impurities from the polymer. The process of this invention, however, involving depolymerization to volatile reaction products and vapor phase stripping in the presence of a solid support matrix, facilitates separation of impurities from polymer, as the desired reaction products are easily carried away by the vapor flow and impurities are trapped and suspended in the solid support material.

The need for the present invention arises because, as the depolymerization step of conventional methods proceeds, the concentration of non-polymer contaminants increases, causing a viscosity increase in the reaction mixture. Gas/liquid contacting is then more difficult and the reaction rate becomes limited. This reaction mass viscosity increase is particularly high when there are present solids with high length to width ratios, approximately greater than 10. (See for example, Metzner, A. B., *Journal of Rheology*, Vol 19, 1985 Issue 6, P739). This occurs because conventional methods operate using a polymer melt system. As melt viscosity increases, the vapor cannot efficiently "bubble" through and adequately contact the polymer. See, for example, EPO Patent Application 0484963A3 and U.S. Pat. No. 5,051,528. Such conventional methods do not overcome the increasing viscosity problem, nor do they address how to handle high levels of solids and contaminants, while also maximizing yield of the desired polymer.

The increasing viscosity problem of conventional methods may be completely avoided, as evidenced by the invention herein, in which the vapor contacting area is maintained in a suspended bed with a supporting solid material, rather than as a liquid or melt. "Suspended bed" describes a reactor content geometry where a solid support is a continuous phase and has sufficient rigidity to maintain a porosity for gas passage, thus developing increased vapor contacting area. A suspended bed may have many phases present including gas, liquids of high and low viscosity, as well as solids.

The use of a solid support can maintain a suspended bed reactor content geometry. The solid support is functioning in a similar way to packing in a packed distillation column. Typical packings for such columns are rigid, inert particles. These particles are shaped to provide the maximum porosity possible, since the flow rate and separation efficiency for packed columns are directly dependent on the porosity. Most column packings are made of ceramics, metals, glass, and even unreactive polymers, since these materials are suitably rigid and inert. (See Ullman's Encyclopedia of Industrial Chemistry, Volume B3, Unit Operations II, Fifth Edition, VCH Publishers, N.Y. (1988), pp. 4–82–84.) These materials have similarly been found suitable for the solid support of this invention.

By keeping the reaction mixture in a predominantly solid state, rather than maintaining it as a complete liquid or melt, with the supporting solid material present, a high surface area for gas/polymer interactions is maintained and subsequently gas/oligomer interactions occur.

The invention provides an improved method of recovering reaction products from polymer scrap resin by subjecting the scrap resin to a depolymerization agent and a vapor-stripping agent in the presence of a supporting material, such that the resulting reaction products are removed from the reactor as a vapor, and non-polymer contaminants remain with the supporting material. Subsequently the reaction products may be filtered or otherwise treated (e.g. using carbon adsorbers) to remove volatile non-polymer contaminants and recovered by conventional techniques, such as distillation or crystallization or directly repolymerized to a high molecular weight polymer. The residue consisting of solid support and non-polymer contaminants, may also be treated so that the solid support may be reused. Typical methods for such regeneration are pyrolysis or oxidation.

Determination of appropriate temperature and pressure conditions for the process of this invention is influenced by two factors: (1) the reaction rates to produce volatile reaction products and (2) the vapor pressures of the volatile reaction products, which is the driving force to remove the volatile reaction products in the vapor phase. Reaction rates are dependent on the specific reaction kinetics for the specific chemical reactions; thus a general statement about temperature and pressures is impractical. The use of catalysts can further complicate this issue. With regard to the removal of volatile reaction products in the vapor phase, basic engineering can be applied and temperature and pressure limits can be determined. For a specific reaction system, goal volatile reaction products can be identified. The least volatile reaction product, usually the one of highest molecular weight, must have a vapor pressure greater than about 0.2% of the total pressure of the system to be efficiently removed, preferably greater than 0.5% of the total pressure, and most preferably greater than about 2.0% of the total pressure. Although lower vapor pressure products may be removed using this invention, the cost of stripping agent recovery and recycle makes recovery of these materials expensive, and therefore only economical if they have a high value. The operating temperature will vary depending on the operating pressure and the partial pressure of the least volatile reaction product. Typically, for methanolysis of PET, the operating pressure can range from about 0 psig (6.9 kPa) to about 500 psig (3447 kPa), most preferably about 50 psig (345 kPa) to about 100 psig (689 kPa), and the operating temperature can range from about 140° C. to about 350° C. most preferably about 220° C. to about 300° C. For glycolysis of PET, the operating pressure can range from high vacuum to about 50 psig (345 kPa), preferably near atmospheric pressure, and the operating temperature can range from about 250° C. to about 350° C., preferably about 300° C. For ammonolysis of polyamides, the operating pressure can be as high as 5000 psig (34,470 kPa), and the temperature generally in the range of about 220° C. to about 350° C. Cycling the reactor between higher pressures for reaction and lower pressure for stripping can also be used, as described below. Also, it may be useful to coat the starting polymer (polyamide) with phosphoric acid to assist in the depolymerization.

For specific polymers with specific contamination there might be less by-product formation if the system is operated at a temperature below the melting point of the polymer (but above the melting point of the monomers). This approach essentially etches the surface of the polymers, thus allowing prompt removal of the reaction products from the system before significant side reactions occur. This etching process might take longer; however, yield of goal products can be improved.

Further, the method of this invention can be combined with other depolymerizing and recovery techniques as described in the technical background above. As discussed above, depolymerization of PET can be accomplished through the use of diols, dicarboxylic acids and corresponding esters, monomers, mono-carboxylic acids and corresponding esters, oligomers, water, alcohols, e.g., methanol, with optional catalysis. Recovery steps can include distillation, precipitation, filtration, carbon adsorption, crystallization, centrifugation, and subsequent repolymerization. To improve reaction rates, as an example, the steps of the proposed process could be combined with various catalysts and/or pretreatment steps, as described above.

In the process of the invention, the reactor is preferably stainless steel, suitable for pressure operation and equipped with an inlet dip tube, a thermocouple, a vent, and a heated jacket. When methanol is used as the depolymerization and stripping agent for polyethylene terephthalate, the reactor is typically operated at approximately 50 psi (345 kPa) and 220°–250° C. Methanol which is fed to the reactor at approximately 300° C., is first vaporized in a high pressure evaporator and then heated in a superheater. The vapor stream product is a mixture of ethylene glycol, methanol and DMT, which can be subsequently separated by: (1) precipitation of DMT, (2) distillation, (3) partial distillation to remove methanol and then repolymerization of the mixture, or (4) filtration to remove undesirable precipitates.

The process of the invention can be practiced in a batch or continuous fashion. For example, the process may be batch, as described in the examples, or continuous if there is continuous feeding of the polymer and discharging of the residual solid from the reactor, similar to a rotary kiln and various continuous drying processes. Examples of batch or continuous equipment suitable for gas/solid contacting operations may be found in Perry, R. H. et al., *Chemical Engineer's Handbook*, 6th Edition, McGraw-Hill, Inc., 1984, specifically, Chapter 20. "Solids Drying and Gas-Solid Systems" provides descriptions of equipment suitable for use in the process of this invention. Suitable equipment includes, but is not limited to, the following: batch furnaces, continuous tunnels, rotary dryers, agitated dryers, gravity dryers, and fluidized bed systems. Additionally, the process can be designed such that the depolymerization and stripping steps are accomplished sequentially. Batch processing can encompass pulsing or cycling the reaction pressure to achieve repetitive depolymerization and stripping steps. Other solid/gas contacting systems are also suitable for use in carrying out the process of this invention.

Pretreatment of the starting polymer often is advantageous and can be accomplished in the presence or in the absence of a solid support. Frequently, the depolymerization process occurs in two dicrete steps: first, breaking down the high molecular weight polymer to a lower molecular weight polymer and, second, depolymerizing the lower molecular weight polymer to simple compounds. There thus exists an induction period. Depolymerization will be facilitated in those cases by pretreatment, which accelerates the rate of depolymerization. In the case of polyesters, this can involve glycolysis, where the polymer is physically blended with ethylene glycol or with ethylene glycol containing a transesterification catalyst and heating this blend to the depolymerization temperature. During pretreatment the starting polymer is broken down to a lower molecular weight polymer. This step can be carried out in solid state either in the depolymerization reactor, as shown in Examples 7 and 8, or in a separate vessel, as shown in Example 9; or in the melt, using polymer processing equipment. See, for example, Frades, J., *Plastic Engineer's Handbook*, 4th Edition, Van Nostrand Reinhold Company, 1976. Typical equipment includes intensive dry mixers, internal intensive batch mixers, continuous mixers and extruders.

The starting polymer, as well as the solid support, can be preheated prior to entering the volatilization reactor to increase the rate of vaporization.

Unless otherwise specified, in Examples 1–30, below, the following reactor set-up was used:

A 1200 ml stainless steel reactor suitable for pressure operation was equipped with an inlet dip tube, a thermocouple, a vapor vent, and an electrically heated jacket. The vent from the reactor was connected to a recovery system.

The experiment was batch with respect to polymer and continuous with respect to the depolymerization and stripping agents. Methanol was used as the depolymerizing and stripping agent.

Additionally, unless otherwise specified, the general process employed in Example 1 was used in subsequent Examples. Further, unless otherwise specified, all parts, proportions, and percentages are by weight.

EXAMPLES

EXAMPLES 1–3: UNFILLED POLYETHYLENE TEREPHTHALATE HOMOPOLYMER

Example 1

Polyester with Insulation Glass

The reactor was charged with 200 g of commercial grade PET homopolymer (DuPont CRYSTAR® 1934, Wilmington, Del.; the same source was used for subsequent examples) and 67 g of insulation glass fibers (CTFSK, 1½ inch (3.81 cm), ¾ PCF FHC 25/50 R-5.2, Certain Teed Corp., Valley Forge, Pa.) which were physically blended. The vessel was heated using the electrically heated jacket. When the internal temperature reached 180° C., hot methanol flow (about 300° C.) was fed into the reactor at about 10 ml/minute (measured as a liquid at room temperature). The methanol was provided from a reservoir, through a positive displacement pump, a steam jacketed evaporator and finally an electrically heated superheater. The vessel temperature rapidly increased and was maintained at goal conditions using the heated jacket. The maximum reaction temperature achieved was about 225° C., below the m.p. of PET but above the melting point of its reaction products. The extent of reaction was monitored by observing the rate of DMT collection. Methanol flow was maintained either for a fixed amount of time or until an observable drop in dimethylterephthalate collection was observed.

In this and the following examples, the reactor residue was weighed and analyzed for DMT and oligomer content as well as for inorganics. The amount of DMT and oligomer was determined by a % acetone insoluble test, since DMT and oligomers dissolve in acetone (up to a molecular weight, Mn, of about 225), but high molecular weight polymers do not. The glass and inorganic content were determined by % ash. From this data, the PET lost in the by-product can be determined. The theoretical residue was calculated from the known composition of the starting material, being the amount of non-polyester material. If the composition was not known, it was measured as described below. The percent polymer conversion is calculated as follows:

$$\text{Conversion} = \frac{\% \text{ Polymer (Total Weight Charged} - \text{actual residue)}}{(\text{Total Weight Charged} - \text{theoretical residue})} \times 100$$

The total weight charged does not include ethylene glycol and catalyst added during pretreatment. A summary of key process variables and sample analysis is presented in Table 1.

The resulting residue clearly demonstrated two distinct phases. A top phase above the dip tube exit that was predominantly glass, and a bottom phase that was below the dip tube exit and predominantly oligomer. After about 11 hours, 55% of the PET was converted.

Example 2

PET with Added Glass Bundles

The reactor was charged with 200 g of PET and 200 g of glass fiber bundles (½ inch (3.81 cm) chopped glass, Owens/Corning Fiberglas Corp., Toledo, Ohio) which were physically blended. The resulting residue clearly demonstrated two distinct phases. A top phase above the dip tube exit that was predominantly glass, and a bottom phase that was below the dip tube exit and predominantly oligomer. After 12.5 hours, 52% of the PET was converted.

Residual material was recovered from the reactor and analyzed for ash content and % insolubles. Results are shown in Table 1.

Example 3

PET with added Glass Fibers

In the reactor 200 g of PET and 100 g of freely divided glass fibers (recovered from Examples 6–11) were physically blended as they were charged to the reactor.

Residual material was recovered from the reactor and analyzed for ash content and % insolubles. Complete conversion of the PET was achieved in 11 hours. Results are shown in Table 1.

Comparative Example A

Pet without Solid Support

The reactor was charged with 200 g of commercial grade PET as unprocessed pellets. The reactor operated at about 221° C. (below the melting point of PET but above the melting point of its monomers) while hot methanol was passed through the polymer.

Residual material was recovered from the reactor and analyzed for ash content and % insolubles. Results, shown in Table 1, indicate that the polymer conversion was not as high as that demonstrated in Examples 1–3.

It should be noted that a limiting feature of the equipment used in the examples of the invention herein, was that the reactor dip tube, used for the introduction of methanol, did not extend to the bottom of the reactor. Approximately 160 ml of reactor volume is below the dip tube. Thus, in runs made without a solid support matrix present, about 170 g of polymer may not be effectively contacted with methanol; the methanol only sweeping past the surface.

Summary Examples 1–3

The introduction of glass fibers in Examples 1–3 increased the conversion of PET to volatile monomers versus Example A where no glass was present. Part of the striking improvement was due to specific reactor geometry (see Note in Ex. A), but this cannot explain the 100% conversion in Example 3.

Examples 4–5

UNFILLED PET WITH POLYETHYLENE

Example 4

Polyethylene (PE)/PET Mixture with Added Glass Fibers

In this example, 100 g PE, 100 g PET and 100 g of glass (recovered from Examples 6–11) were charged to the reactor. Complete conversion of the PET was achieved in 6 hours. The residual appearance was uniform glass with concentrated areas of PE distributed uniformly. Due to the higher PE levels the residue was not free flowing.

Residual material was recovered from the reactor and analyzed for ash content and % insolubles. Results are shown in Table 1.

Example 5

PE/PET Mixture with Added Glass Fibers

In this example, 40 g PE, 160 g PET and 100 g of glass (recovered from Examples 6–11 ) were charged to the reactor. Complete conversion of PET was achieved in 5 hours. The residue appearance was uniform free flowing glass with concentrated areas of PE that were distributed uniformly.

Residual material was recovered from the reactor and analyzed for ash content and % insolubles. Results are shown in Table 1.

Comparative Example B

Polyethylene (PE)/PET Mixture

In this example, 40 g polyethylene (Oxychem, Dallas, Tex.) and 160 g PET were charged to the reactor that was heated to 282° C. with 10 ml/min methanol flow. After 9 hours, 170 grams of material remained. The resulting residue clearly demonstrated two distinct phases. A top phase was predominantly PE and a bottom phase was predominantly polyester.

Residual material was recovered from the reactor and analyzed for ash content and % insolubles. Results, shown in Table 1, indicate that the polymer conversion was not as good as Example 5, which used the same polymer mixture but incorporated a solid support.

Comparative Example C

PE/PET Mixture

In this example, 100 g PE and 100 g PET were charged to the reactor that was heated to 282° C. with 10 ml/min methanol flow. After 9 hours, 196 g remain. Again the two phases were observed, a PE top phase and a bottom polyester phase.

Residual material was recovered from the reactor and analyzed for ash content and % insolubles. Results, shown in Table 1, indicate that the polymer conversion was not as good as Example 4, which used the same polymer mixture but incorporated a solid support.

Summary Examples 4–5

Introduction of glass fibers in Examples 4 and 5 improve conversion of polyester to monomers, compared to Comparative Examples B and C.

Examples 6–11

FILLED PET—WITH VARIOUS PRE-TREATMENTS AND PROCESS CONDITIONS

Example 6

Filled PET

This example employs PET in which the support material is part of the starting material. Experimental polyester/glass composite parts, containing about 72% PET, 25% chopped glass fibers (same fibers as Example 2), and the balance being modifiers, were ground and screened through a ⅛ inch screen. 400 grams of the ground material were charged to the reactor. After 16 hours, 170 grams of residue were extracted and was analyzed for ash content and % insolubles. Results are shown in Table 1.

Example 7

Filled Polyester with Ethylene Glycol Pretreatment

In this example, 400 grams of the ground material (from Example 6) were physically blended with 32 grams of ethylene glycol (Polyester Grade Product Code 35227, Union Carbide Chemicals and Plastics Co., Inc., Danbury, Conn.) prior to charging the reactor. Standard heat-up and operating procedures were followed. After 12 hours of operation, 138 grams of residue were extracted and analyzed for ash content and % insolubles. Results are shown in Table 1.

Example 8

Example 7 Treatment with Catalyst Solution

In this example, 400 grams of the ground material (from Example 6) were physically blended with 33 grams of ethylene glycol and tetra butyl titanate (TBT) (2.5%) (DuPont TYZOR® TBT, Wilmington, Del.) solution prior to charging the reactor. Standard heat-up and operating procedures were followed. After 7 hours of operation, 113 grams of residue remained which were found to contain 90.8% ash.

Residual material was also analyzed for % insolubles. Results are shown in Table 1.

Example 9

Example 8 Treatment with Preheating

In this example, 400 grams of the ground material (from Example 6) were physically blended with 33 grams of ethylene glycol/TBT catalyst (2.5 %) solution. The mixture was then pretreated by placing in a rotary evaporator and gently tumbled while heating to 150° C. and maintaining that temperature for 4 hours. The mixture was then charged to the reactor. Standard heat-up and operating procedures were followed. After 5 hours of operation, 115 g of residue remained, containing 90.2% ash.

Residual material was also analyzed for % insolubles. Results are shown in Table 1.

Example 10

Example 8 Treatment with increased MeOH Flow

Here, Example 8 was repeated except the methanol flow rate was increased to 20 ml/min. Reaction was completed in 4 hours with similar extraction and ash content.

Residual material was recovered from the reactor and analyzed for ash content and % insolubles. Results are shown in Table 1.

Example 11

Example 8 at 100 psi

Here, Example 8 was repeated but the pressure was increased to 100 psi. After 7 hours of operation, 110 grams of residue remained which were found to contain 87% ash.

Residual material was also analyzed for % insolubles. Results are shown in Table 1.

Summary: Examples 6–11

Examples 6 through 11 demonstrate the advantage of treating the polymer to initiate depolymerization. Introduction of ethylene glycol and catalyst accelerates the depolymerization process. The higher methanol flow rate in Example 10 increased the stripping capacity of the system. Operating at a higher pressure improved conversion slightly.

Examples 12–15

FILLED AND UNFILLED PET MIXTURES WITH CATALYST TREATMENT

Example 12

Filled: PET/Unfilled, Contaminated PET with Catalyst Solution

In this example, 100 g of ground material (from Example 6), 225 g PET and 12 g ethylene glycol/TBT catalyst solution (5% catalyst) were physically blended then charged to the reactor. After 11 hours, essentially all of the polyester was extracted.

Residual material was recovered from the reactor and analyzed for ash content and % insolubles. Ash content of the residue was found to be 88%. Results are shown in Table 1.

Example 13

Filled PET/Unfilled PET with Catalyst Solution

In this example, 200 g ground material (from Example 6), 200 g PET and 16 g ethylene glycol/TBT catalyst solution (5%) were charged to the reactor. After 8 hours, essentially all of the polyester was extracted.

Residual material was recovered from the reactor and analyzed for ash content and % insolubles. Ash content of the residue was 90.3%. Results are shown in Table 1.

Example 14

Filled PET/PET Oligomer with Catalyst Solution

In this example, 280 g of ground material (from Example 6), 90 g of PET oligomer from a commercial facility (degree of polymerization, $D_p$, was about 5–10) and 12 g TBT catalyst solution (5%) were charged to the reactor. After 9 hours, essentially all of the polyester was extracted.

Residual material was recovered from the reactor and analyzed for ash content and % insolubles. Ash content of residue was found to be 90.8%. Results are shown in Table 1.

Comparative Example D

PET Oligomer with Catalyst Solution

In this example, 300 grams of PET oligomer (same as Example 14) and 12 g of ethylene glycol/TBT catalyst (5%) solution were charged to the reactor. After 11 hours, all of the charged material was reacted. No residual material was left.

Example 15

Filled PET/PET By-Product with Catalyst Solution

In this example, 100 g of ground material (from Example 6), 225 g of a PET residue from a large scale methanolysis Market Development Facility (MDF) and 12 g ethylene glycol/TBT catalyst solution (5%) were charged to the reactor. After 11 hours, most of the PET was extracted.

Residual material was recovered from the reactor and analyzed for ash content and % insolubles. Ash content of residue was found to be 83.5%. Results are shown in Table 1.

Comparative Example E

PET By-Product with Catalyst Solution

In this example, 300 grams of a PET residue from a Market Development Facility (MDF) and 12 g of ethylene glycol/TBT catalyst (5%) solution were charged to the reactor. After 12 hours the majority of the polyester was extracted.

Residual material was recovered from the reactor and analyzed for ash content and % insolubles. Results are shown in Table 1.

Summary: Examples 12–15

Examples 12 through 15 demonstrate using glass filled PET as a support material to recover other PET. Example 12 and 13 demonstrate essentially complete conversion of PET versus Example A, where only 14% was converted. In Example 14, a low molecular weight oligomer was recovered faster than in Example D. It is interesting to note by comparison that in Example D the oligomer was completely converted, while Example A, the high molecular weight polymer, was not. This demonstrates that reducing the initial molecular weight is advantageous. In Example 15, additional monomers were recovered from residue obtained from a liquid phase methanoloysis facility. When the residue was methanolysized separately in Example E, a viscous tar residue was obtained at low yields.

Example 16

PBT with Glass

In this example, 300 g polybutyleneterephthalate and glass (50/50 blend of Celanese 6407 and 6500, Hoechst Celanese Corp., Chatham, N.J.), and 24.8 g of EG/TBT catalyst (2.5%) solution were charged to the reactor.

Residual material was recovered from the reactor and analyzed for ash content and % insolubles. Results are shown in Table 1.

Examples 17–20

USE OF VARIOUS STRIPPING AGENTS

Example 17

Ethylene Glycol as Stripping Agent

In this example, ethylene glycol was used as a depolymerizing and stripping agent. The volatile component generated in this example is bis-b-hydroxyethyl-terephthlate. 100 grams of ground material (from Example 6) was charged to the reactor. Reactor pressure was set at 0 PSIG. Ethylene glycol was fed at 10 ml/min when the reactor temperature reached 220° C. Heating was continued to 296° C. Conditions were held for 13 hours.

Residual material was recovered from the reactor and analyzed for ash content and % insolubles. Results are shown in Table 1.

Example 18

Treatment of Example 17, with Nitrogen Added for Stripping

Example 17 was repeated with nitrogen added to assist with the stripping. 100 grams of ground material (from Example 6)was charged to the reactor. Reactor pressure was set at 0 PSIG. Ethylene glycol was fed at 10 ml/min (measured at ambient conditions) when the reactor temperature reached 220° C. Nitrogen was fed at 140 ml/min, measured at ambient conditions. Conditions were held for 12 hours.

Residual material was recovered from the reactor and analyzed for ash content and % insolubles. Results are shown in Table 1.

Example 19

MeOH/Ethylene Glycol Mixture as Stripping Agent

In this example, a 90/10 mixture of ethylene glycol and methanol was used as the depolymerization and stripping agent. The volatile components generated in this example are DMT, EG and bis-b-hydroxyethyl terephthalate. 400 grams of ground material (from Example 6) were charged to the reactor. Reactor pressure was set at 50 PSIG. The methanol/ethylene glycol mixture was fed at 10 ml/min when the reactor temperature reached 225° C. The maximum reaction temperature reached was 236° C. and conditions were held for 12 hours.

Residual material was recovered from the reactor and analyzed for ash content and % insolubles. Results are shown in Table 1.

Example 20

Example 19 at Higher Temperature

In this example, Example 19 was repeated but the maximum reaction temperature reached was 287° C. and conditions were held for 12 hours.

Residual material was recovered from the reactor and analyzed for ash content and % insolubles. Results are shown in Table 1.

Example 21

Two-Step Stripping—EG then Methanol

In this example, Example 8 was repeated but stripping was accomplished by first feeding EG at 5 ml/min for 20 minutes, followed by methanol at 10 ml/min for the remainder of 9 hours. A slight improvement in DMT recovery rate was achieved over Example 8.

Residual material was recovered from the reactor and analyzed for ash content and % insolubles. Results are shown in Table 1.

Example 22

PET Carpet

Commercial PET carpet (34 oz, 963.9 g; 0.6 in, 1.52 cm, pile height from Evans Black, a Division of Shaw Industries, Dalton, Ga.), 200 g, was cut into 1 inch (2.54 cm) squares and charged to the reactor. After 12 hours of methanol feed, 117 g of residue was recovered and analyzed for ash content. Results are shown in Table 1.

Example 23

PET Carpet Pretreated by Catalyzed Glycolysis

Cut carpet (same as in Example 22), 200 g, was physically blended with 20 g of a 2.5% solution of TYZOR®TPT (DuPont Company tetrapropyl titanate) in ethylene glycol. The blend was charged to the reactor and exposed to methanol vapors for 12 hours. The recovered residue, which weighed 109 g, was analyzed for ash content. Results are shown in Table 1. DMT recovery was observed to occur earlier and at a higher rate than in Example 22.

Example 24

PPT with Glass

Experimental polyester/glass composite parts, containing about 60% of PPT and about 40% of chopped glass fibers (same fibers as used in Example 2) were ground and passed through a screen having a hole size of 0.375 in (0.95 cm). The ground material, 300 g, was charged to the reactor. After feeding methanol for 12 hours, 103 g of residue was recovered and analyzed for ash content. Results are shown in Table 1.

Example 25

PPT with Glass and Catalyzed Glycol Solution

Ground material from Example 24, 190 g, was physically blended with 16 g of catalyzed ethylene glycol solution (2.5 wt % TYZOR®TPT in ethylene glycol). The blend was charged to the reactor and exposed to methanol vapors for 12 hours. The recovered residue, 72 g, was analyzed for ash content. Results are shown in Table 1. DMT recovery was observed to occur earlier and at a higher rate than in Example 2,4.

Example 26

PPT Carpet

A PPT carpet was approximated by physically blending 53 g of PPT carpet fibers with 111 g of carpet backing physically separated from a PET carpet. The blend was charged to the reactor and exposed to methanol vapors for 12 hours. The recovered residue which weighed 87 g, was analyzed for ash content. Results are shown in Table 1.

Example 27

PPT Carpet With Catalyzed Glycolysis Pretreatment

A PPT carpet was approximated by physically blending 56 g of PPT carpet fibers with 144 g of carpet backing from a PET carpet. To this blend was added 20 g of a 2.5% TYZOR®TPT solution in ethylene glycol. The resulting physical blend was charged to the reactor and exposed to methanol vapors for 12 hours. The recovered residue, weighing 117 g, was analyzed for ash content. Results are shown in Table 1. DMT recovery was observed to occur earlier and at a higher rate than in Example 26.

Comparative Example F

PPT

PPT pellets, 200 g, were charged to the reactor. After 12 hours of feeding methanol, 83 g of residue was recovered and analyzed for ash content. Results are shown in Table 1.

Example 28

Glass-filed LCP (I)

Glass-filled LCP (ZENITE® 6130, DuPont, Wilmington, Del.), 300 g, was charged to the reactor and exposed to methanol vapors for 12 hours. The recovered residue, 110 g, was analyzed for ash content. Results are shown in Table 1.

Example 29

Glass-filled LCP (I) with Catalyzed Glycolysis Pretreatment

Glass-filled LCP (ZENITE® 6130), 300 g, and 30 g of catalyzed ethylene glycol solution (2.5 wt % TYZOR®TPT in ethylene glycol) were physically blended and charged to the reactor. After 12 hours of methanol exposure 116.7 g of residue were recovered and analyzed for ash. Results are shown in Table 1. Volatile reaction products were observed to occur earlier and at a higher rate than in Example 28.

Comparative Example G

LCP

In this example, 200 g of LCP (ZENITE® 6000, DuPont, Wilmington, Del.) was charged to the reactor. After 12 hours of feeding methanol, 144 g of residue was recovered and analyzed for ash content. Results are shown in Table 1. ZENITE® 6000 is a composition of the LCP of ZENITE® 6130 filled with 30% of glass fibers.

Example 30

Glass-filled LCP (II) with Catalyzed Glycolysis Pretreatment

Glass-filled LCP (VECTRA®C130, Hoechst Celanese, Spartanburg, S.C.), 300 g, and 20 g of a 2.5% TYZOR®TPT solution in ethylene glycol were physically blended and charged to the reactor. After 12 hours of methanol exposure, 98 g of residue was recovered and analyzed for ash content. Results are shown in Table 1. Volatile reaction products were observed to form at rates similar to those in Example 29.

Example 31

Glass-Filled Polyamide

This example was carried out in a 1000-ml stainless steel reactor suitable for pressure operation and equipped with a bottom inlet, two thermocouples, a vent and an electrically heated jacket. The vent was connected to a recovery system.

The experiment was batch with respect to polymer and continuous with respect to ammonia, which was the depolymerization and stripping agent.

The reactor was charged with 500 g of 33% glass-filled nylon 6,6 (ZYTEL® 70G33, DuPont, Wilmington, Del.). Prior to charging, the pellets were coated with 20 ml of a 2% aqueous solution of phosphoric acid. The reactor was heated with the electrical heater, and ammonia preheated to the reactor temperature was passed through the reactor from the bottom inlet at a rate of 23 ml/min (measured at room temperature and 200 psi; 1379 kPa). The exit flow from the reactor was restricted to maintain an operating pressure of 4000 psi (27,579 kPa). The temperature in the reactor was maintained at 230° C. for the first 5 hours and 240° C. for the next 4 hours. The extent of reaction was monitored by the observed rate of volatile product collection.

The product, which solidified on cooling, was analyzed to be a mixture of hexamethylenediamine, cyanovaleramide, and nylon dimers and oligomers. The reactor residue showed the polymer still in the shape of pellets with glass fibers protruding from the surface. From the weight of reactor residue the polymer conversion after 9 hours was calculated by the method described in Example 1 as 67%.

Comparative Example H

Polyamide

The reactor set-up and the general process employed were the same as in Example 31. The reactor was charged with 335 g of nylon 6,6 (DuPont, Kingston, Ontario, Canada) that had been coated with 9 ml of a 2% aqueous solution of phosphoric acid. The ammonia flow rate was 22 ml/min.; the reaction pressure was 4000 psi 27,579 kPa); and the reaction temperature was 230° C. for the first 5 hours and 240° C. for the next 4 hours. The volatile reaction products were the same as in Example 31. The reactor residue was a fused solid with numerous pores present. From the weight of reactor residue, the polymer conversion after 9 hours was calculated as 36%.

TABLE 1

PERCENTAGE POLYMER CONVERSION
(All runs at 10 ml MeOH/min, 50 psig, unless noted)

| EX. | MeOH Flow (hrs) | Max Temp (°C) | Total Charge* (grams) | Theoret. Residue (grams) | Actual Residue (grams) | % Polymer Conversion | Residue analysis % ash | % acetone insolub. | Charge Description |
|---|---|---|---|---|---|---|---|---|---|
| 1 | 11 | 234 | 267 | 67 | 157 | 55 | NA | NA | PET & INSULATION GLASS |
| 2 | 12.5 | 230 | 400 | 200 | 296 | 52 | 72 | 79.7 | PET & GLASS BUNDLES |
| 3 | 11 | 226 | 300 | 100 | 99 | 100 | 90.56 | 99.3 | PET & RECOVERED GLASS |
| A | 8 | 221 | 200 | 0.2 | 173 | 14 | 0 | 84.5 | PET |
| 4 | 6 | 287 | 300 | 200 | 195 | 105 | 90.26 | 99.1 | 100PE/100PET/100R GLASS |
| 5 | 5 | 280 | 300 | 140 | 136 | 102 | 88.55 | 98.5 | 40PE/160PET/100R GLASS |
| B | 9 | 282 | 200 | 40 | 170 | 19 | 0.19 | 99 | 40PE/160PET |
| C | 9 | 282 | 200 | 100 | 196 | 4 | 0 | 99.4 | 100PE/100PET |
| 6 | 16 | 227 | 400 | 112 | 170 | 80 | 64.04 | 82.08 | Ground Composite |
| 7 | 12 | 227 | 400 | 112 | 138 | 91 | 76.68 | 88.72 | Ex. 6 & EG |
| 8 | 7 | 233 | 400 | 112 | 113 | 100 | 90.84 | 99.51 | Ex. 6 & EG & TBT |
| 9 | 5 | 233 | 400 | 112 | 115 | 99 | 90.24 | 99.29 | Ex. 6 & EG & TBT-PRETREAT |
| 10 | 4 | 241 | 400 | 112 | 104 | 103 | 89.39 | 99.36 | Ex. 6 & EG & TBT-20 CC/MIN |
| 11 | 7 | 248 | 400 | 112 | 110 | 100 | 87.19 | 99.95 | Ex. 6 + EG + TBT – 100 PSI |
| 12 | 11 | 227 | 325 | 28 | 29 | 100 | 88.12 | 98.89 | 100 Ex. 6/225PET/EG + TBT |
| 13 | 8 | 227 | 400 | 56 | 61 | 99 | 90.28 | 99.3 | 200 Ex. 6/200PET/EG/TBT |
| 14 | 9 | 228 | 370 | 78 | 63 | 105 | 90.86 | 99.1 | 280Ex. 6/90OH/EG/TBT |
| D | 11 | 225 | 300 | 0.3 | 0 | 100 | N/A | N/A | 300OH/EG/TBT |
| 15 | 11 | 230 | 325 | 50 | 38.5 | 104 | 83.5 | 94.6 | 100Ex. 6/225MDF/EG/TBT |
| E | 12 | 228 | 300 | 30 | 100 | 75 | 1.34 | 16.64 | 300MDF/EG/TBT |
| 16 | 12 | 267 | 300 | 99.3 | 103 | 98 | 84.6 | 99.1 | PBT(GLASS)/EG/TBT |
| 17 | 13 | 296 | 100 | 28 | 48 | 72 | 64.86 | 99.6 | 10 cc EG/Ex. 6 0 psig |
| 18 | 12 | 302 | 100 | 28 | 39 | 85 | 60.9 | 99.5 | 10 cc EG-N$_2$/Ex. 6 0 psig |
| 19 | 12 | 236 | 400 | 112 | 229 | 59 | 44.96 | 73.2 | 90/10 MeOH/EG/Ex. 6 |
| 20 | 12 | 287 | 400 | 112 | 110.4 | 100 | 89.56 | 99.1 | 90/10 MeOH/EG/Ex. 6 |
| 21 | 9 | 235 | 400 | 112 | 112 | 100 | 86.6 | 99.2 | 400 Ex. 6/EG/TBT EG then MeOH |
| 22 | 12 | 225 | 200 | 104 | 117 | 86 | 37.6 | NA | PET Carpet |
| 23 | 6 | 227 | 200 | 104 | 109 | 94 | 49.47 | NA | PET Carpet & EG & TPT |
| 24 | 12 | 225 | 300 | 114 | 103 | 106 | 98.68 | NA | PPT ground composite |
| 25 | 12 | 226 | 190 | 72.6 | 72 | 101 | 99.13 | NA | Ex. 24 & EG & TPT |
| 26 | 12 | 224 | 164 | 85 | 87 | 97 | 68.75 | NA | PPT Carpet |
| 27 | 6 | 227 | 200 | 104 | 117 | 86 | 45.13 | NA | PPT Carpet & EG & TPT |
| F | 12 | 222 | 200 | 0 | 83 | 59 | 0 | NA | PPT |
| 28 | 12 | 312 | 300 | 107 | 110 | 98 | 96.6 | NA | Glass-filled LCP (I) |
| 29 | 12 | 313 | 300 | 107 | 116.7 | 95 | 89.81 | NA | Ex. 28 & EG & TPT |
| G | 12 | 318 | 200 | 0 | 144 | 28 | 0 | NA | LCP |
| 30 | 12 | 312 | 300 | 91 | 98 | 97 | 94.43 | NA | Glass-filled LCP (II) |
| 31 | 9** | 240 | 500 | 167 | 277 | 67 | 61 | NA | Glass-filled Polyamide 6,6 |
| H | 9** | 240 | 335 | 0 | 213 | 36 | 2.5 | NA | Polyamide 6,6 |

*Excluding ethylene glycol and catalyst added during pretreatment
**Ammonia flow as shown in Examples

DETERMINATION OF THEORETICAL RESIDUE IN POLYESTER DEPOLYMERIZATION

For the most part, theoretical residue was determined from the known composition of a particular sample (see Example 1). In situations where the composition was not known, the following method was used to estimate theoretical residue.

Into a 400-ml stainless steel vessel designed for high pressure and temperature was placed 237 g of methanol, 12 g of polymer, and 0.05 g of tetrabutyl titanate catalyst. Using an external electric heater, the vessel was heated to 250° C. and maintained at this temperature for 2 hours. Pressure in the vessel was allowed to build without venting (about 1400 psig; 9653 kPa). The vessel was allowed to cool to room temperature and was discharged.

The resulting suspension was filtered to collect the solids. (At room temperature DMT has a solubility in methanol of about 0.7%, and ethylene glycol is fully miscible. The solubility of DMT in mixtures of methanol with ethylene glycol is slightly higher.)

The solids were dried and the dry weight was noted. At this point, a major part of the solids was DMT.

The solids were then suspended in acetone, taken in an amount such as to give a dissolved solids concentration of 2%, and agitated. DMT and oligomers (up to about 225 number average molecular weight) are soluble in acetone at room temperature. The suspension was filtered and the remaining insoluble solids were dried and weighed. The solid material collected at this point was not considered to be a polyester. The amount of this material was considered to be "theoretical residue" for the polymer.

This "theoretical residue" estimate is conservatively low since some additives and modifiers that are soluble in methanol or acetone are not included in the estimate. However, these additives and modifiers may remain with the residue during methanolysis with vapor phase separation of reaction products. To gain additional understanding, the acetone-insoluble residue is ashed to determine inorganic content.

What is claimed is:

1. Process for recovering reaction products from a reaction mass that comprises a starting polymer which is at least one member of the group consisting of polyesters, polyamides, and polyesteramides having about 2% to 70% by weight of non-polymer contaminants, which process comprises:
- (a) depolymerizing the polymer by means of a depolymerization agent to yield volatile reaction products;
- (b) vapor-phase stripping the volatile reaction products, to yield a stripping agent/product distillate;
  wherein said reaction mass in said depolymerizing and stripping steps comprises from about 5% to about 99% by weight of the reaction mass of a solid support, which solid support is solid under the conditions of steps (a) and (b) and forms a suspended bed, either the quantity or both the quantity and the rate of recovery of reaction products being enhanced over that obtained in the absence of said solid support; and
- (c) recovering the reaction products from the stripping agent/product distillate while leaving non-volatile residue material with the support material.

2. The process of claim 1 wherein the starting polymer comprises repeat units selected from the group of repeat units derived from at least one of the following classes (a), (b), and (c):
- (a) at least one difunctional acid selected from the group consisting of dicarboxylic acids and carbonic acid and at least one other difunctional compound selected from the group consisting of diols and diamines; or
- (b) at least one substituted carboxylic acid selected from the group consisting of hydroxycarboxylic acids and aminocarboxylic acids; or
- (c) at least one difunctional acid selected from the group consisting of dicarboxylic acids and carbonic acid, at least one other difunctional compound selected from the group consisting of diols and diamines, and at least one substituted carboxylic acid selected from the group consisting of hydroxycarboxylic acids and aminocarboxylic acids.

3. The process of claim 2 wherein the starting polymer is selected from the group consisting of polyesters based on aromatic dicarboxylic acids, aliphatic polyamides, aramids, polycarbonates, polyesteramides, and liquid crystal copolyesters and copolyesteramides.

4. The process of claim 3 wherein the starting polymer is selected from the group consisting of polyethylene terephthalate, poly(1,3-propylene) terephthalate, poly(1,4-butylene) terephthalate, nylon 6, and nylon 6,6.

5. The process of claim 1 wherein the depolymerization agent is selected from the group consisting of oligomers of polyesters and polyamides; alcohols; alkanediols; aromatic and aliphatic dicarboxylic acids and their diesters and monoesters; ammonia; monoamines; diamines; and water.

6. The process of claim 1 wherein said depolymerization and stripping are conducted within a temperature range of about 140° C. to about 350° C.

7. The process of claim 6 wherein the starting polymer is a polyamide, and the depolymerization step is conducted at a pressure of about 5000 psig. (34,475 kPa) or less.

8. The process of claim 6 wherein the stripping agent is selected from the group consisting of nitrogen, alcohols, alkanediols, and ammonia.

9. The process of claim 1 wherein the solid support is a material selected from the group consisting of glass, carbon fibers, minerals, metals, ceramics, wood, aramid polymers and non-depolymerized residual polymer.

10. The process of claim 6 wherein the starting polymer is a polyester and the pressure in the reactor during depolymerization is 1000 psig (6890 kPa) or less.

11. The process of claim 10 wherein methanol is both the depolymerizing agent and the stripping agent; the temperature is about 220° C. to about 300° C.; and the pressure is atmospheric to about 200 psig (1378 kPa).

12. The process of claim 1 which is a batch process.

13. The process of claim 1 which is a continuous process.

14. The process of claim 2 wherein the solid support is a component of the starting charge or feed.

15. The process of claim 14 wherein the solid support is fused to the polyester or polyamide.

16. The process of claim 1 wherein the solid support is preheated.

17. The process of claim 1 which is carried out at a temperature below the melting temperature of the starting polymer.

18. The process of claim 1 wherein the suspended bed of solid support is fluidized.

19. The process of claim 1 wherein the suspended bed of solid support is stirred.

20. The process of claim 1 wherein the starting polymer is a polyester, and the process includes a pretreatment of the starting polymer by glycolysis in the presence or absence of a catalyst, said pretreatment comprising blending the starting polymer with ethylene glycol, either neat or containing a catalyst dissolved therein, and heating said blend to the depolymerization temperature.

* * * * *